(12) United States Patent
Ganey et al.

(10) Patent No.: US 8,679,189 B1
(45) Date of Patent: Mar. 25, 2014

(54) BONE GROWTH ENHANCING IMPLANT

(71) Applicants: Amendia Inc., Marietta, GA (US); The Aerospace Corporation, El Segundo, CA (US)

(72) Inventors: Timothy Ganey, Tampa, FL (US); Frank Edward Livingston, Redondo Beach, CA (US)

(73) Assignees: Amendia Inc., Marietta, GA (US); The Aerospace Corporation, El Segundo, CA (US)

( * ) Notice: Subject to any disclaimer, the term of this patent is extended or adjusted under 35 U.S.C. 154(b) by 0 days.

(21) Appl. No.: 13/767,055

(22) Filed: Feb. 14, 2013

Related U.S. Application Data

(60) Provisional application No. 61/763,223, filed on Feb. 11, 2013.

(51) Int. Cl.
*A61F 2/28* (2006.01)

(52) U.S. Cl.
USPC ..................................................... 623/23.49

(58) Field of Classification Search
USPC .......... 623/23.49, 23.72–23.76, 16.11, 11.11, 623/17.11, 17.16, 18.11
See application file for complete search history.

(56) References Cited

U.S. PATENT DOCUMENTS

| | | | | |
|---|---|---|---|---|
| 3,745,995 A * | 7/1973 | Kraus | ............................... | 602/2 |
| 3,820,534 A * | 6/1974 | Kraus et al. | ............................ | 2/2 |
| 4,195,367 A * | 4/1980 | Kraus | ......................... | 623/23.49 |
| 4,214,322 A * | 7/1980 | Kraus | ......................... | 623/23.49 |
| 4,978,323 A * | 12/1990 | Freedman | ....................... | 600/12 |
| 5,030,236 A * | 7/1991 | Dean | .......................... | 623/23.49 |
| 5,032,129 A * | 7/1991 | Kurze et al. | ................. | 623/23.49 |
| 5,163,958 A * | 11/1992 | Pinchuk | ..................... | 623/23.49 |
| 5,383,935 A * | 1/1995 | Shirkhanzadeh | .......... | 623/23.49 |
| 5,456,724 A * | 10/1995 | Yen et al. | ................... | 623/23.49 |
| 5,976,187 A * | 11/1999 | Richelsoph | ................ | 623/17.16 |
| 6,034,295 A * | 3/2000 | Rehberg et al. | ............. | 623/23.49 |
| 6,080,155 A * | 6/2000 | Michelson | .................. | 606/86 A |
| 6,083,264 A * | 7/2000 | Wood et al. | ................ | 623/23.56 |
| 6,120,502 A * | 9/2000 | Michelson | ................... | 606/247 |
| 6,123,705 A * | 9/2000 | Michelson | ................... | 623/17.16 |
| 6,143,036 A * | 11/2000 | Comfort | .................... | 623/23.54 |
| 6,149,650 A * | 11/2000 | Michelson | ................. | 623/17.16 |
| 6,387,096 B1 * | 5/2002 | Hyde, Jr. | ......................... | 606/60 |
| 6,481,440 B2 * | 11/2002 | Gielen et al. | .................. | 128/898 |
| 6,602,296 B1 * | 8/2003 | Day et al. | ................... | 623/23.49 |
| 6,605,089 B1 * | 8/2003 | Michelson | ....................... | 606/32 |
| 6,627,321 B1 * | 9/2003 | Ellingsen et al. | ............. | 428/469 |
| 6,712,853 B2 * | 3/2004 | Kuslich | ....................... | 623/17.16 |
| 7,179,295 B2 * | 2/2007 | Kovacevic | ................. | 623/17.15 |
| 7,455,672 B2 * | 11/2008 | Michelson | ....................... | 606/60 |
| 7,579,077 B2 * | 8/2009 | Dubrow et al. | ............... | 428/357 |
| 7,708,778 B2 * | 5/2010 | Gordon et al. | ............. | 623/17.15 |
| 7,824,444 B2 * | 11/2010 | Biscup et al. | ............. | 623/17.12 |
| 8,075,630 B2 * | 12/2011 | Ricci et al. | .................. | 623/23.74 |
| 8,197,551 B2 * | 6/2012 | Swain et al. | ............... | 623/23.49 |
| 8,273,610 B2 * | 9/2012 | Or-Bach et al. | ............... | 438/142 |
| 2003/0040806 A1 * | 2/2003 | MacDonald | ............... | 623/23.49 |

(Continued)

*Primary Examiner* — Alvin J. Stewart
(74) *Attorney, Agent, or Firm* — David L. King

(57) ABSTRACT

An implant device having a non-conductive base structure with at least two exposed or exterior surfaces wherein at least one of the exposed or exterior surfaces has attained electrical conductivity on at least portions of the surface by an energy exposure wherein portions of the exposed or exterior surfaces are transformed by the energy exposure to attain the electrical conductivity.

21 Claims, 12 Drawing Sheets

(56) References Cited

U.S. PATENT DOCUMENTS

| | | | |
|---|---|---|---|
| 2003/0083746 A1* | 5/2003 | Kuslich | 623/17.11 |
| 2005/0228503 A1* | 10/2005 | Gundolf | 623/22.21 |
| 2005/0256586 A1* | 11/2005 | Kraus et al. | 623/23.16 |
| 2006/0089642 A1* | 4/2006 | Diaz et al. | 606/60 |
| 2006/0137688 A1* | 6/2006 | Aisenbrey | 128/205.25 |
| 2006/0159916 A1* | 7/2006 | Dubrow et al. | 428/357 |
| 2006/0184211 A1* | 8/2006 | Gaunt et al. | 607/48 |
| 2006/0241766 A1* | 10/2006 | Felton et al. | 623/17.12 |
| 2006/0293724 A1* | 12/2006 | Kronberg et al. | 607/51 |
| 2007/0073300 A1* | 3/2007 | Attawia et al. | 606/73 |
| 2007/0141106 A1* | 6/2007 | Bonutti et al. | 424/423 |
| 2009/0088857 A1* | 4/2009 | Michelson | 623/17.16 |
| 2009/0125099 A1* | 5/2009 | Weber et al. | 623/1.34 |
| 2009/0163981 A1* | 6/2009 | Stevenson et al. | 607/63 |
| 2009/0243756 A1* | 10/2009 | Stevenson et al. | 333/172 |
| 2009/0273353 A1* | 11/2009 | Kroh et al. | 324/655 |
| 2009/0292344 A1* | 11/2009 | Lowry et al. | 607/116 |
| 2009/0326602 A1* | 12/2009 | Glukhovsky et al. | 607/41 |
| 2010/0028387 A1* | 2/2010 | Balasundaram et al. | 424/400 |
| 2010/0140160 A1* | 6/2010 | Dubrow et al. | 210/348 |
| 2010/0168867 A1* | 7/2010 | Swain et al. | 623/23.49 |
| 2011/0021899 A1* | 1/2011 | Arps et al. | 600/372 |
| 2011/0034975 A1* | 2/2011 | Ferree | 607/105 |
| 2011/0048770 A1* | 3/2011 | Reiterer et al. | 174/152 GM |
| 2011/0054582 A1* | 3/2011 | Dabney et al. | 607/116 |
| 2011/0060419 A1* | 3/2011 | Choi et al. | 623/23.49 |
| 2011/0245924 A1* | 10/2011 | Kuslich et al. | 623/17.16 |
| 2011/0288468 A1* | 11/2011 | Dadd et al. | 604/21 |
| 2012/0003463 A1* | 1/2012 | Dry | 428/305.5 |
| 2012/0009391 A1* | 1/2012 | Dry | 428/188 |
| 2012/0058100 A1* | 3/2012 | Shastri et al. | 424/94.4 |
| 2012/0071979 A1* | 3/2012 | Zipnick | 623/17.16 |
| 2012/0095558 A1* | 4/2012 | Wooley et al. | 623/16.11 |
| 2012/0185047 A1* | 7/2012 | Wooley | 623/17.16 |
| 2012/0232330 A1* | 9/2012 | Geiges | 600/13 |
| 2012/0248595 A1* | 10/2012 | Or-Bach et al. | 257/706 |
| 2012/0251835 A1* | 10/2012 | Dry | 428/454 |
| 2012/0259264 A1* | 10/2012 | Swain et al. | 604/9 |
| 2012/0277812 A1* | 11/2012 | Kraus et al. | 606/86 R |
| 2012/0296190 A1* | 11/2012 | Kondabatni et al. | 600/373 |
| 2012/0302821 A1* | 11/2012 | Burnett | 600/14 |
| 2012/0309237 A1* | 12/2012 | Marzano et al. | 439/675 |
| 2012/0316482 A1* | 12/2012 | Karim | 602/5 |
| 2013/0023794 A1* | 1/2013 | Stein et al. | 600/587 |
| 2013/0110114 A1* | 5/2013 | Gomaa et al. | 606/91 |
| 2013/0166039 A1* | 6/2013 | Shaw-Klein | 623/23.49 |
| 2013/0226025 A1* | 8/2013 | Bourlion et al. | 600/547 |
| 2013/0226273 A1* | 8/2013 | Dabney et al. | 607/116 |
| 2013/0244121 A1* | 9/2013 | Gogotsi et al. | 429/338 |
| 2013/0245736 A1* | 9/2013 | Alexander et al. | 607/116 |
| 2013/0253297 A1* | 9/2013 | Johnson et al. | 600/373 |

* cited by examiner

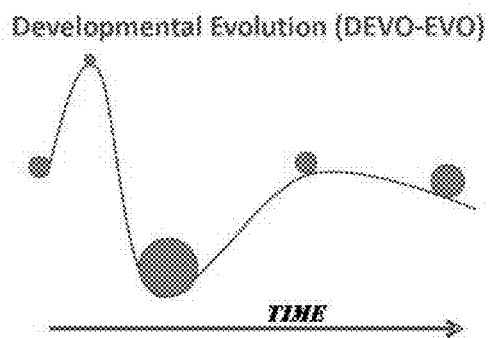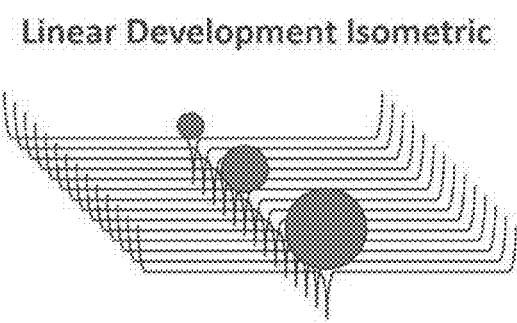
FIG. 7A                FIG. 7B
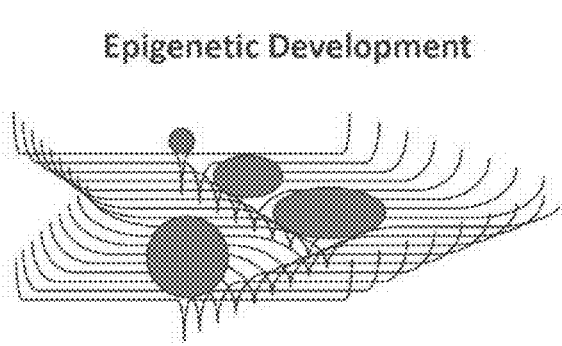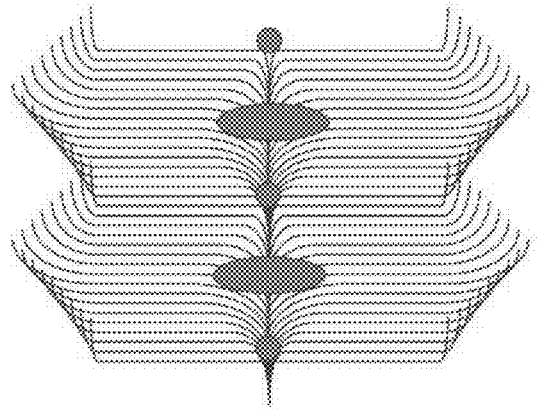
FIG. 7C
FIG. 7D

BONE GROWTH ENHANCING IMPLANT

TECHNICAL FIELD

The present invention relates to implants generally, more particularly to implant devices that have enhanced surface features that extend 3-dimensionally into the base structure of the implant at least several microns to stimulate new bone growth formation on and into the implant.

BACKGROUND OF THE INVENTION

The use of skeletal implants is common in surgical repairs. Implants are employed in a variety of procedures such as spinal repair, knees, hips or shoulders and others. A common and most important feature of many implants is the integration of the implant into the skeletal structure. Mechanical fasteners, surface modifications, coatings, sutures and adhesives and other ways of affixing the device to the bone structure are used. These implants can be fashioned from human bone or other biological material or alternatively can be made from implantable grade synthetic plastics, ceramics or metals like stainless steel, titanium or the alloys of metals suitable for implantation.

One of the benefits of these plastic or metal implants is the strength and structure can be specifically designed to be even more durable than the bone being replaced.

As mentioned, one concern is properly securing the implant in place and insuring it cannot be dislodged or moved after repair. One of the best solutions to this issue is to allow the surrounding bone structure to grow around the implant and in some cases of hollow bone implants to allow new bone growth to occur not only around, but throughout the implant as well to achieve interlocked connectivity. Enhancing surface area by blasting, etching, or in some other way increasing the relative surface energy interface with the biologic component is desirable.

This is not particularly easy in many of the metal implants or hard plastic implants. In fact, the surface structure of the implant material is often adverse to bone formation. On some implant surfaces this may in fact be a desirable characteristic, but in those procedures where new bone growth formation is desirable this is problematic.

It is therefore an object of the present invention to provide an improved implant device that encourages new bone growth formation at selected surfaces of the device. The selected surfaces can be some or all external or internal exposed surface features of the implant device. The device with exposed surfaces that have selected surfaces for bone growth formation can be prepared by the methods as described below.

In addition to better activate a natural cellular response to new bone creation, it is a further object of the present invention to achieve an electrical conductivity at the surface of this improved implant device to react to low voltage stimulation which the body of a mammal naturally generates. While electrical conductivity is achieved in many metal implants such as titanium, it is not in plastics or allograft bone implants. It is therefore an object to create surface conductors in otherwise non-conductive implant materials.

SUMMARY OF THE INVENTION

An implant device having a non-conductive base structure with at least two exposed or exterior surfaces wherein at least one of the exposed or exterior surfaces has attained electrical conductivity on at least portions of the surface by an energy exposure wherein portions of the exposed or exterior surfaces are transformed by the energy exposure to attain the electrical conductivity.

Preferably, the non-conductive base structure receives the energy exposure in the form of a spectrum of wavelengths in the visible or non-visible range sufficient to create a material composition change to the base structure at the exposed or exterior surfaces.

Additionally, the energy exposure can be either thermal or non-thermal in its reaction with the implant, yet still manifest change in either geometric or physic-chemical properties.

This material change preferably results in a formation of conductive carbon paths or patterns formed as channels of conductive carbon residue extending at the surface to a depth of 1 to 2 or more microns.

The base structure is preferably made of an organic carbon or hydrocarbon base material synthetically produced such as a polymer of a plastic material or even a ceramic composition. The body structure can be made of an implantable grade synthetic plastic, which is a thermoplastic or thermoset material. The plastic material can be any implantable grade material such as PEEK (polyether ether ketone), PEKK (polyether ketone ketone), polyethylene, ultra high molecular weight polyethylene, polyphenylsulfone, polysulfone, polythermide, acetal copolymer, polyester woven or solid or implantable grade lennite UHME-PE or other suitable implant material or alternatively can be a naturally occurring material such as an allograft bone tissue used for implantation in a mammal. The implant device may include anchoring holes to secure the device to the skeletal structure with fasteners or alternatively can simply be held in place by and between adjacent skeletal structures. The implant device can be built by additive fabrication through a process offering reproducible and reconcilable formation to the isotropic domains inherent to the marine mammal cancellous bone. In such application, the internal structure is modeled for strength, neutralized for strain, and open to surface modification of its entire network of trabecular permutations.

Additional modulations can be represented by material landscapes that in scope and function offer either jointly, or separately landscapes of potential seeded by either geometric, conductivity, resistivity, or combinations of surface mimetic and conductivity variations; in essence electric impedance topography.

The energy used to create the conductive paths or patterns can come from a laser source or other energy source such as a focused acoustic lens, wherein the emitted wavelength can impinge the surface to create a chemical transformation to achieve conductive carbon residue paths or patterns. Lasers are one example of devices that might provide such an energy source; their use extended in a reduced oxygen environment, in an oxygen-purged environment, in inert gasses such as Argon, or in atmospheric conditions so as to create discrete conductive paths in the absence of surface scorching. This insures the base structure is only made conductive at the paths or patterns leaving the rest of the base structure unaltered.

The conductive paths preferably are formed in interconnected networks to allow electrical current to flow along the surface. These paths are small, preferably from a few microns up to several hundred microns wide and formed in discrete channels at the surface extending to a depth of a few microns. These conductive paths react electrically to the low voltages carried by cells to enhance new bone formation at the surface of the implant device. The feature of electro-dynamic field in defining both spatial and physical fate for system evolution has been espoused since Burr (1937). Preferably, the paths have a resistivity under 500 ohms, and in some applications may conform to resistance at the milliohm layer. Ideally, the conductive paths are well below 500 ohms in the range of less than 500 milliohms to a few milliohms. At 500 ohms or less electrically conductive cellular benefits are expected to be achieved at the implant surface.

In addition, the enhanced implant device may also have a 3-dimensional surface texture of voids at exposed surfaces that provide cell attachment locations in addition to the conductive paths wherein the combination accelerates new bone formation.

This enhanced implant device can be made by a method of providing a non-conductive base structure of an implant having exterior or exposed surfaces and exposing at least one or more of the surfaces to an energy source to transform those portions of the base structure into electrically conductive paths or networks.

This transformation further can include the steps of using a laser beam in an oxygen reduced environment to create amorphous carbon channels to form the conductive paths or networks.

This 3-dimensional surface, with characteristic exposed surfaces offers value to the invention in that while resistance is generally inversely proportional to the cross sectional area, the shape of the material imbues additional contact surfaces that enable the attachment to biomaterials without the dilution of a resistivity because of sustained surface conductivity. As such, this material defines in scope and scale electrical domains that fashion specific properties in context of morphology and milieu of the healing environment.

DEFINITIONS

As used herein and in the claims:

"Exposed surface" means surfaces that are typically an outer or planar feature of 2-dimensions as used herein and throughout this description. "Exposed surface" means an outer skin or surface having a depth providing a 3-dimensional character, this depth being the distance the surface pattern penetrates into the body structure of the device to produce a repeatable pattern for enhancing bone formation on the implant device. The exposed surface might also include an open trabecular structure wherein the voids extend from the surface throughout the structure. The exposed surface might also be defined in 4 dimensions, wherein time imposes specific and characteristic metabolic deposits which functionally mature the surface and guide phenotypic responses that are resonant with differentiated tissues and structures.

"Fractal Dimension" as used herein means repeating and sustaining self-similarity.

"Mimetic patterns" mean to mimic a natural or man made or conceived pattern with the capability to replicate these patterns at an exposed surface to at least a depth sufficient to replicate at least the pattern.

BRIEF DESCRIPTION OF THE DRAWINGS

The invention will be described by way of example and with reference to the accompanying drawings in which:

FIGS. 7A-7D represent various schematic representations: FIG. 7A being a Developmental Evolution (Devo-Evo) over time; FIG. 7B being a Linear Development Isometric; FIG. 7C being an Epigenitic Development and FIG. 7D being a Morphology Development.

DETAILED DESCRIPTION OF THE INVENTION

Figure 1:
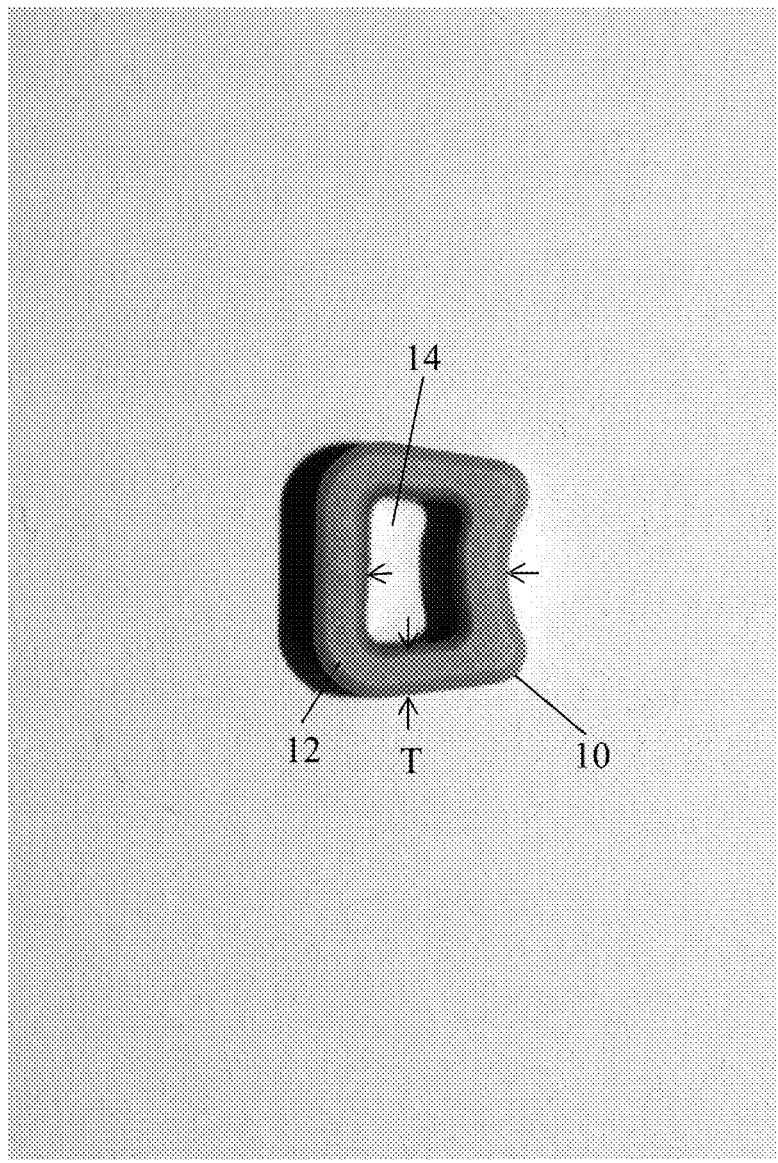
FIG. 1 is a perspective view of an exemplary implant device showing a non-conductive base structure as formed.

Cell membranes are made up of opposing pairs of phospholipids, a specialized type of fat, and loose proteins. Each phospholipid molecule has a ball on one end that works as an electron conductor and two legs that work as electron insulators. These conductors and insulators form a capacitor whose purpose is to store electrons. In effect, the membrane functions as a small battery that stores voltage for the cell. In multicellular animals, the cell membrane also separates the cytoplasm inside the cell from that in the extracellular matrix, maintaining a normal resting membrane polarity that is tissue and organ specific. This potential difference in voltage across the membrane is attributable and maintained by various ion pump proteins that are located in the lipid raft material. The passive electrical properties of a material held between two plane-parallel electrodes of area (A) separated by a distance (d) are completely characterised by the measured electrical capacitance C (units Farads) and conductance G (units Ohm" or Siemens), The conductivity U is the proportionality factor between the electric current density and the electric field, and is a measure of the ease with which 'delocalised' charge carriers can move through the material under the influence of the field. For aqueous biological materials, the conductivity arises mainly from the mobility of hydrated ions.

All of the energy generated for the use of a cell occurs within the mitochondria via a type of rechargeable battery system known as ATP/ADP. ATP exists when the battery is charged and ready for work. As energy is spent, the battery becomes ADP. Recharging takes place as electrons are brought in from the cell membrane and mixed with a small amount of phosphorus. This process takes place approximately 70 times per day in every cell in the body. If the ATP/ADP system is not functioning properly, cells cannot generate the power they need to keep the body working. In addition, when the number of mitochondria that are supposed to be functioning in a cell is reduced for any reason, the cell's ability to provide for its own energy needs is diminished. The battery is used to maintain the pumps, to sustain the equilibrium of the cell, and to serve as a biophysical set point for cell maintenance. It also plays a significant role in maintaining specific cell phenotype, aligning cell genetic machinery, and in sustaining active cell metabolic activity specific to the cell and tissue of account.

This greatly oversimplified description of the human body as an electrical power source provides an interesting insight into how the body generates new growth in bone. Cells migrate to the wound in the region of a non-union fracture and create new bone formations to heal the break, offering connectivity in an effort to sustain voltage and reduce the flow of current. Health stems from organized capacitance and a loss of voltage accompanied by a flow of current has been shown to negatively impact wound healing and other biologic processes.

In the case of bone implants, it is often equally important that new bone growth occur around the implant device to insure it is a stable structure safely secured in the skeletal structure to which it is affixed. During this healing process, it is very desirable to have new bone growth to start as soon as possible and to rapidly surround the implanted device.

To achieve this rapid bone growth, the present inventor developed a way to improve the exposed surfaces of an implant by creating repeating patterns of voids in an implant device. In that invention entitled "Bone Implants And Method Of Manufacture" filed on Nov. 23, 2011 application Ser. No. 13/303,944 which is incorporated herein in its entirety, he found he could create devices that were "mimetic" that is simulated the morphology of human or mammal bone tissue at least from the exposed surfaces to a depth of a few microns to several hundred microns in polymer type implants.

Recently, during the development and refinement of processes to create these mimetic patterns, a new and useful discovery has been made which provides for the basis of the present disclosure of an enhanced bone growth implant device made from a non-conductive base structure wherein a conductive transformation is created at an exposed surface by exposure to an energy source. This ability to create electrical conductivity at the surface of the implant device will enhance the cells ability to generate new bone growth formation around these surfaces and improve healing time.

With reference to the FIGS. 1-4, an exemplary implant device is shown. Lasers were used based on maskless scripts that were functionally correlated with imaging that was able to translate micro-CT surface morphology and coordinate a binary script that could be varied in location, pulse duration, and pulse number in real time to effect depth, width, and confluence of pattern onto and within hydrocarbon structures. Laser based surface enhancement has several options and can be used in variegated domain sizes, obtain structures and topographies designed to optimize synergies accentuating epigenetic domains, and detail diverse physical and chemical properties that yield interconnected networks of cooperative and autonomous systems. These complex functionalities and compositions offer a physics-based mimetic that are an indivisible asset of biologic entities.

Laser process is termed "gene-scripted" or "genotype-coded" which refers by analogy to the paired process of hybrid reading frames inherent to DNA biology. By example, both the process script defining intensity and the tool path code couplets that can occupy a common reading frame, enable authorization for expression, and enhancement of pattern based on script intention. Variations in duration and pulse number offer reproducible patterns, defined geometries, compositional fidelity, and variation in topology with resolution ranging in multiple nanometer metrics.

With reference to FIG. 1, an exemplary implant device is shown. The implant device 10 is structured to position in the skeletal vertebrae of a mammal. As shown, the implant device has an exterior surface 12 and a hollow opening 14. As shown, the implant 10 has a generally uniform wall thickness T. The actual shape of the implant is not particularly important to the present invention, but rather the exterior surfaces that are in contact with the skeletal tissue are the focus of this invention.

Figure 1A:
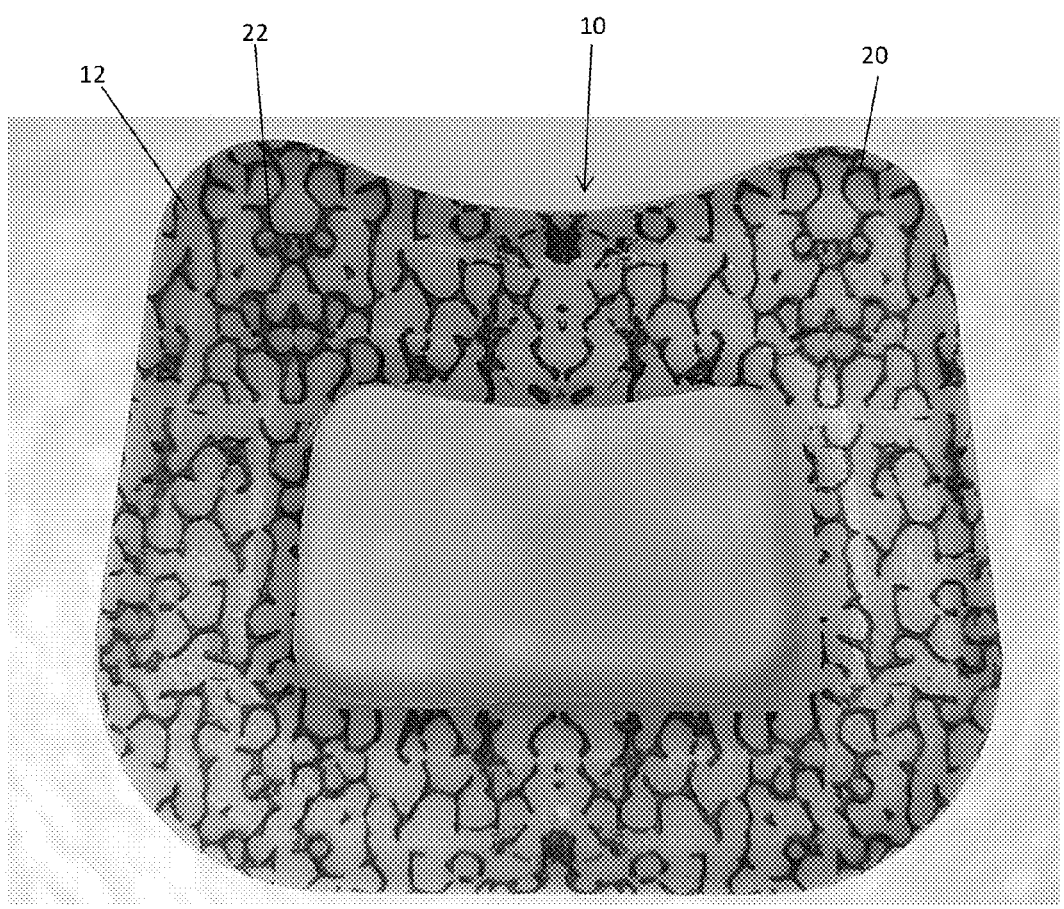
FIG. 1A is a perspective view of the exemplary implant device made according to the present invention after being transformed at the exterior or exposed surfaces by exposure to an energy source to form conductive paths or networks on portions of the surface.

In FIG. 1A, the implant device 10 has had the exterior surfaces 12 altered dramatically by incorporating paths 20 and networks 22 that appear black at the surfaces 12. As shown, all the exposed surfaces 12 have these paths or networks. Alternatively, it is possible to add these features in selected areas if so desired.

Figure 1B:
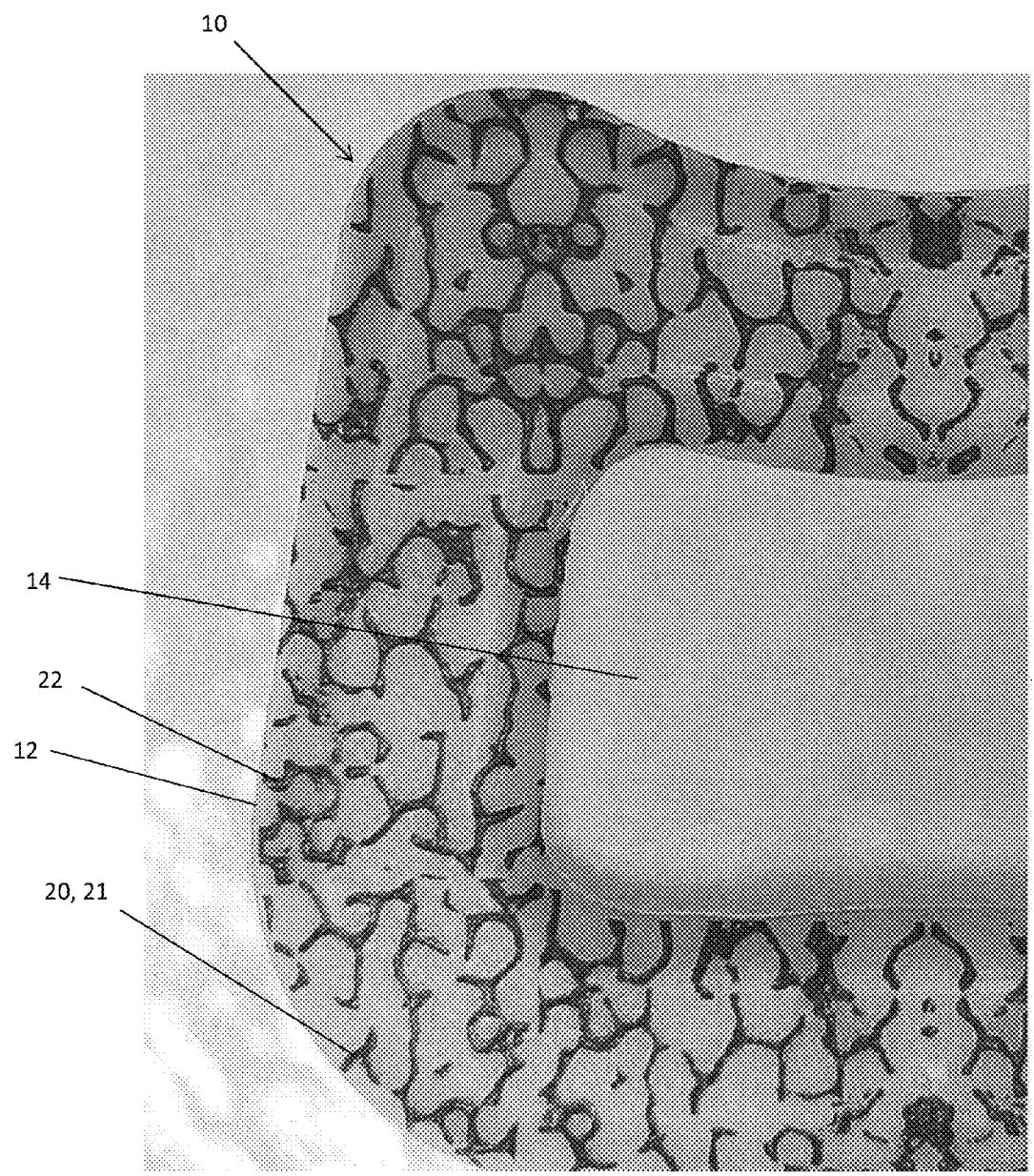
FIG. 1B is an enlarged view of the device of FIG. 1A.
Figure 2:
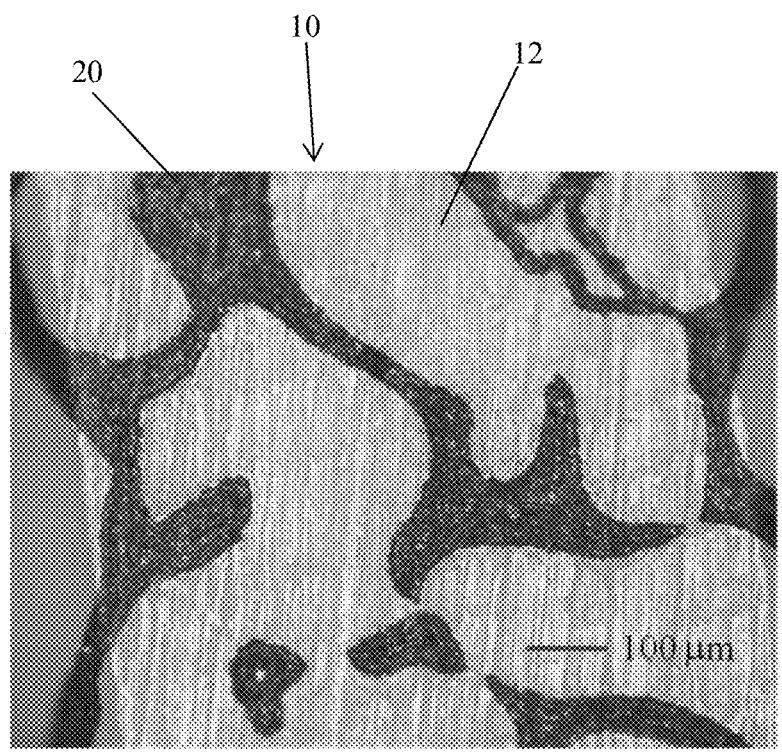
FIG. 2 shows a small portion of the conductive path or network magnified showing the scale bar of 100 microns is shown in lower right corner.
Figure 3A:
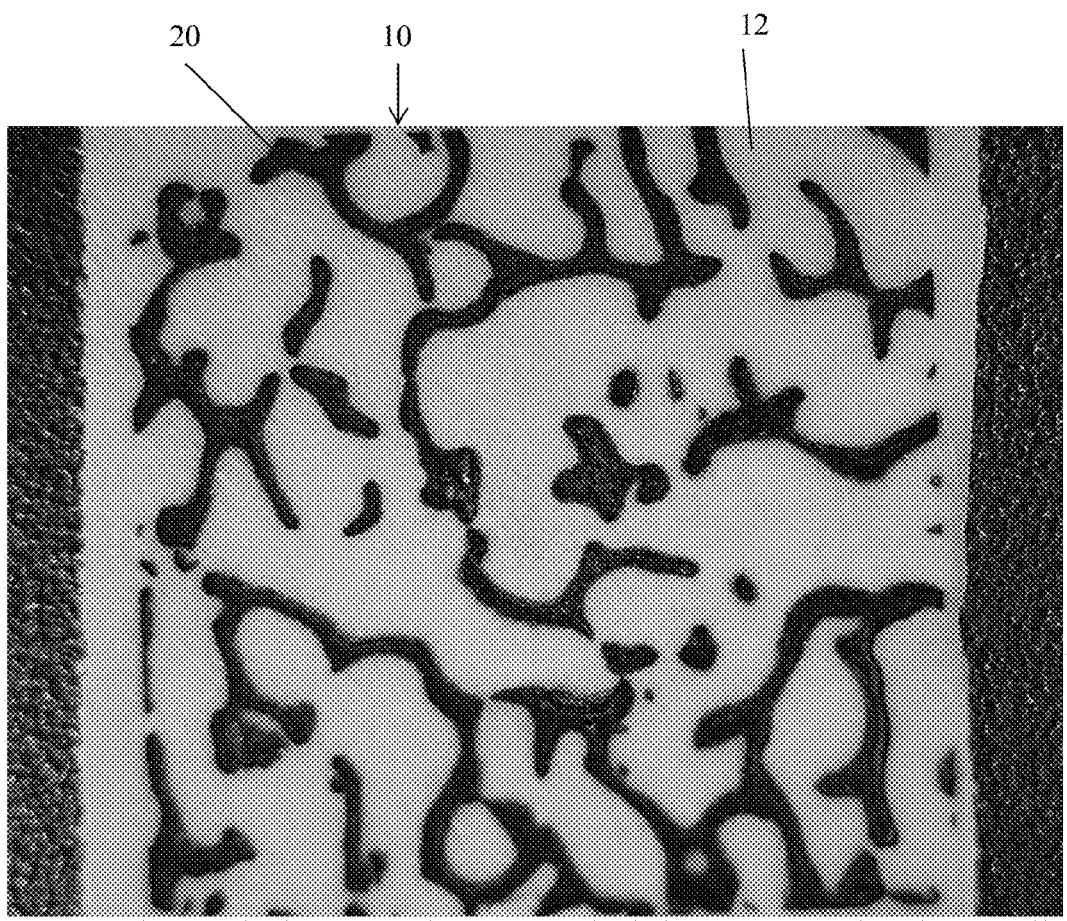
FIGS. 3A-3D are views showing portions of the device with progressive magnification of the conductive paths or networks.
Figure 3B:
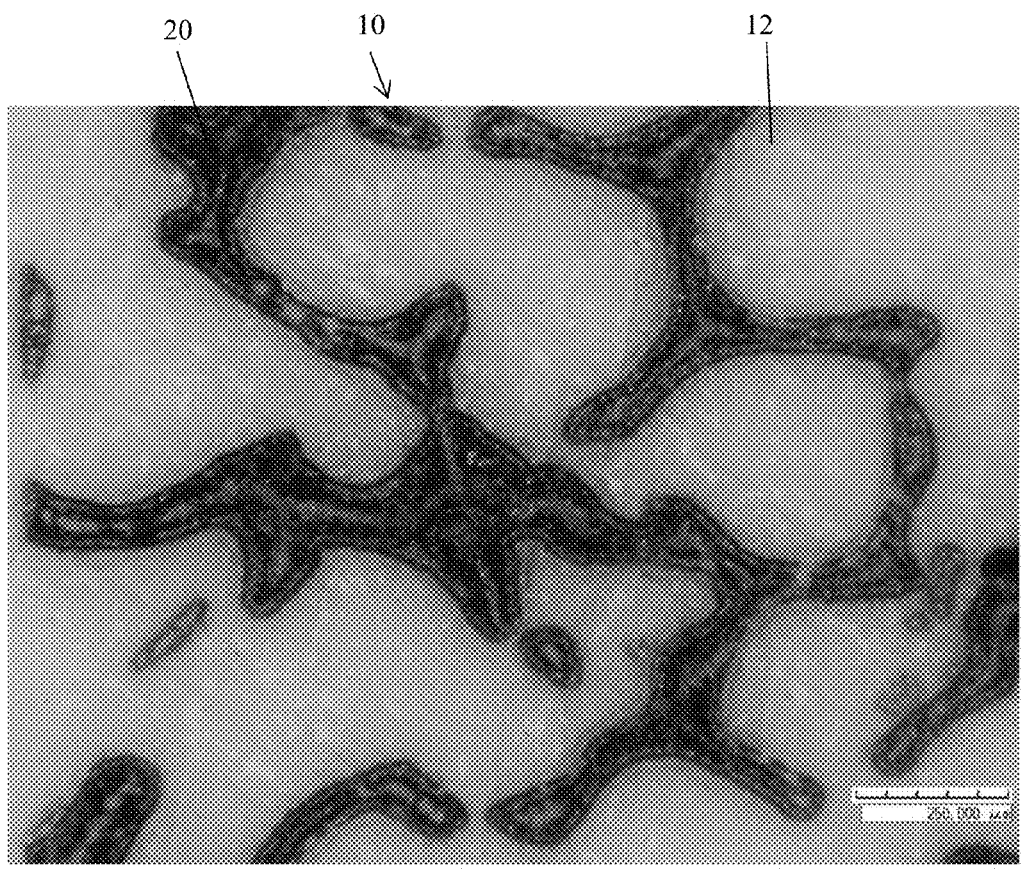
Figure 3C:
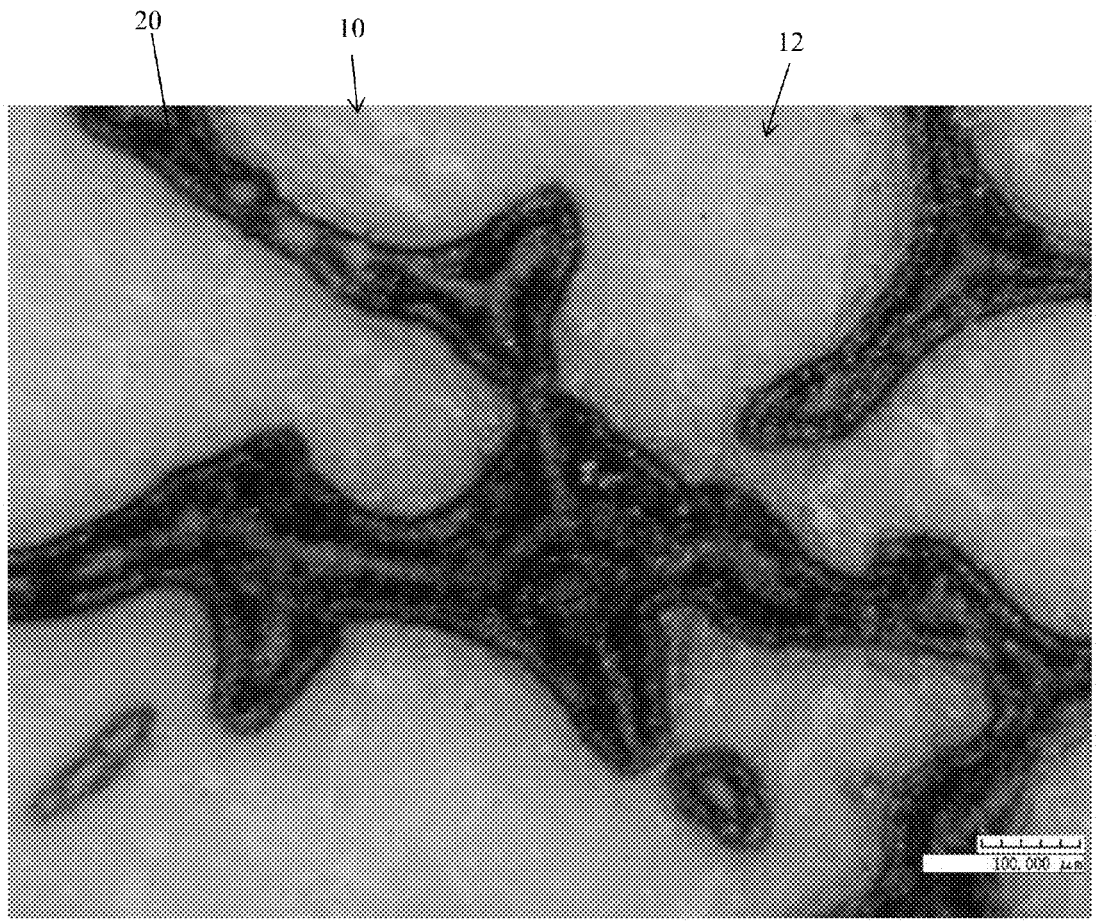
Figure 3D:
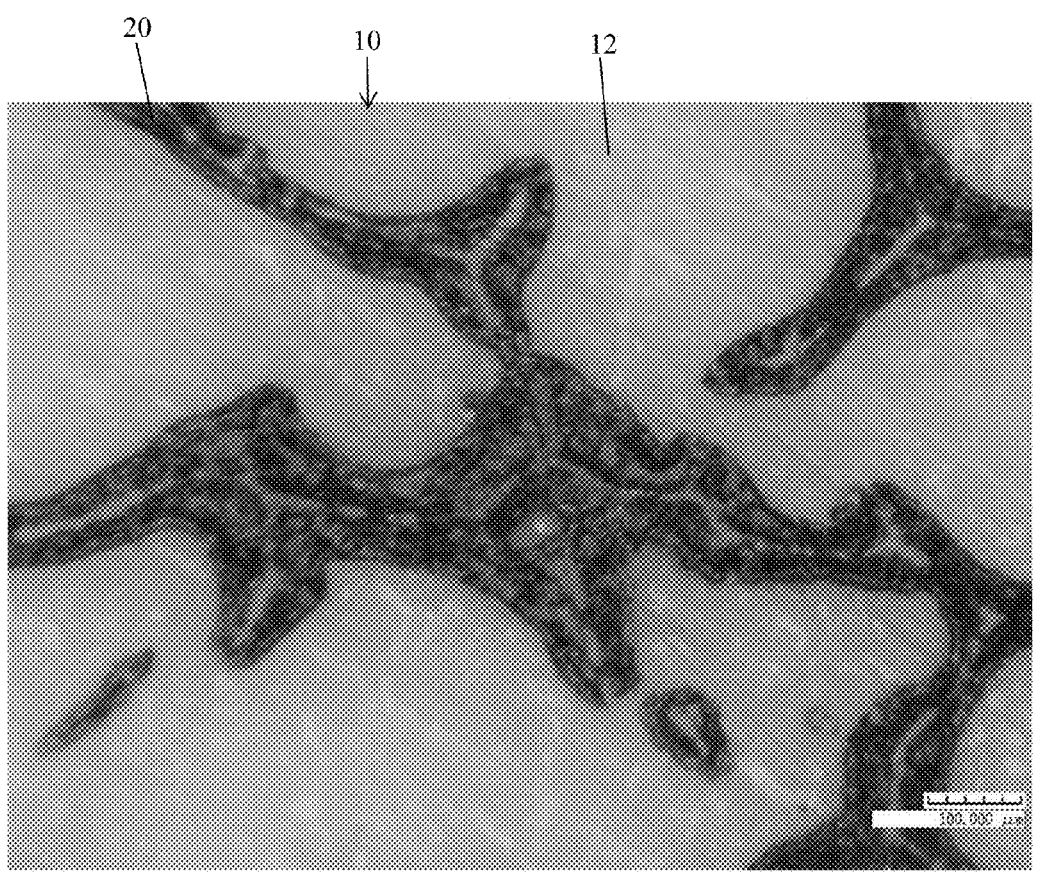

With reference to FIG. 1B, an enlarged portion of the implant device 10 of FIG. 1A is shown. The black paths 20 or network 22 of paths 20 are more clearly visible. These blackened features are conductive carbon residue formed from the material of the implant 10, in this example the material is a plastic, PEEK material. The carbon conductive paths were formed by exposure to an energy source. The energy source in this example was a laser pulse focused to create channels 21 in the base material at 120K pulses per second. The channels 21 left a residue of conductive carbon in the channel. This conductive carbon material is the result of transforming the base material, in this case PEEK, to carbon in channels at least 2 to 3 microns deep into the implant from the exterior surface.

With reference to FIGS. 2, 3A, 3B and 3C; progressively larger magnifications of the conductive path 20 is shown. These views show that at even very high resolution the conductive carbon path coats paths 20 in the channel 21 almost completely. This insures the otherwise non-conductive material has been completely transformed into a conductive network 22 of carbon paths 20. As shown, the conductive paths 20 and networks 22 were shown occupying about 20 to 30 percent of the exposed surface. It is possible to achieve effective conductivity at lower percentages such a few percent 1 or 2 percent or at higher percentages up to 100 percent, however, it is believed preferable to have a range of 15 to 50 percent to allow for electrical conductivity while maintaining regions of electrically insulated regions. The remarkable benefit of the creation of carbon paths at the surface is electrically conductive material is created without the addition of a conductive layer or coating or a separate dispersion of electrically conductive material. In a plastic implant to provide electrically conductive features would have typically required adding it in the material at molding. This results in embedding conductive material deep into the implant when all the new bone growth formation starts at the surface. The present invention achieves high levels of conductivity where needed and avoids the costs of blending the conductive material in the implant, but rather creates conductivity from the base material.

Figure 4:
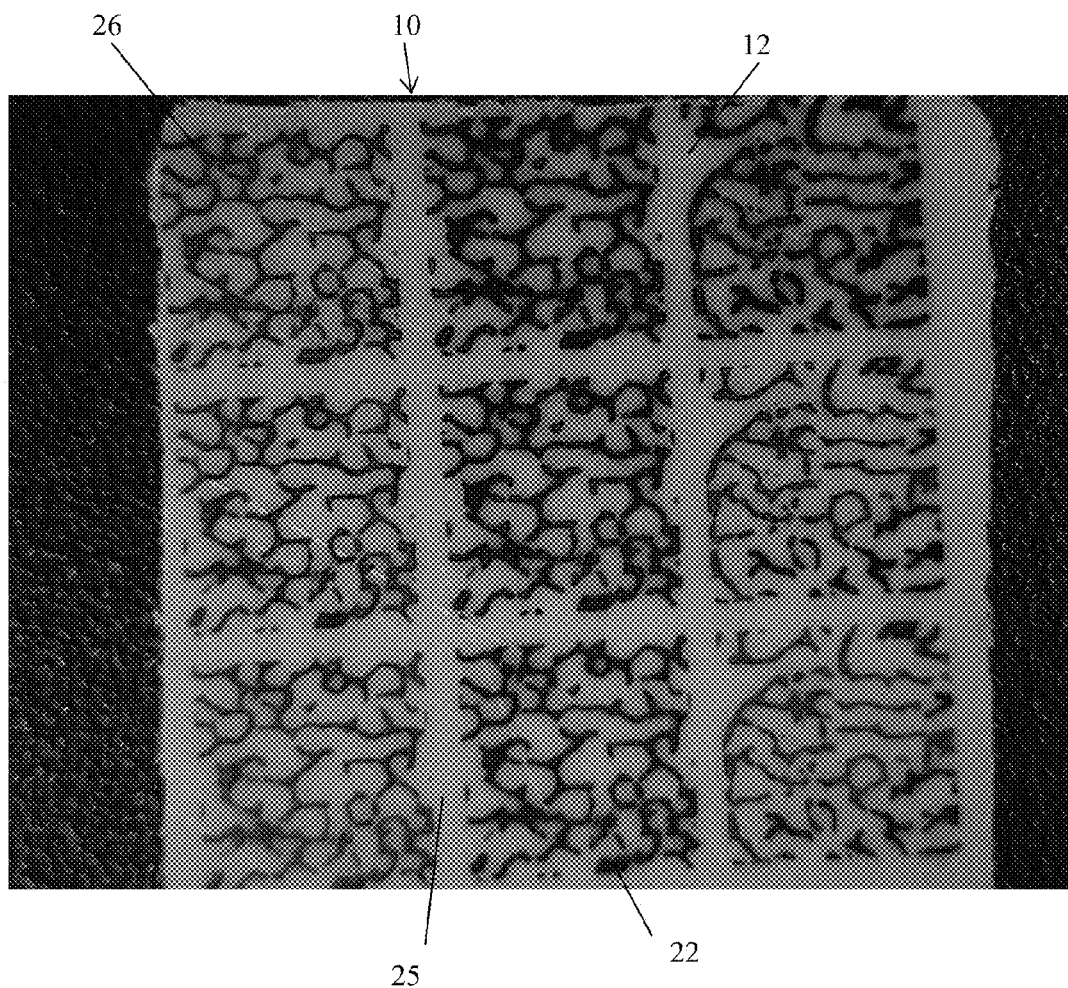
FIG. 4 is a view showing a plurality of identical conductive networks replicated on a surface with spaces or boundaries provided so the repeatability of the pattern can be illustrated.

With reference to FIG. 4, an example of a plurality of repeating conductive pattern networks 22 are shown spaced by non-conductive borders 25. This implant 10 surface 12 exhibits the ability to form electrically conductive grids 26 from networks 22. The benefits of such grids 26 would allow a low current to be delivered to isolated surfaces if so desired.

Figure 5:
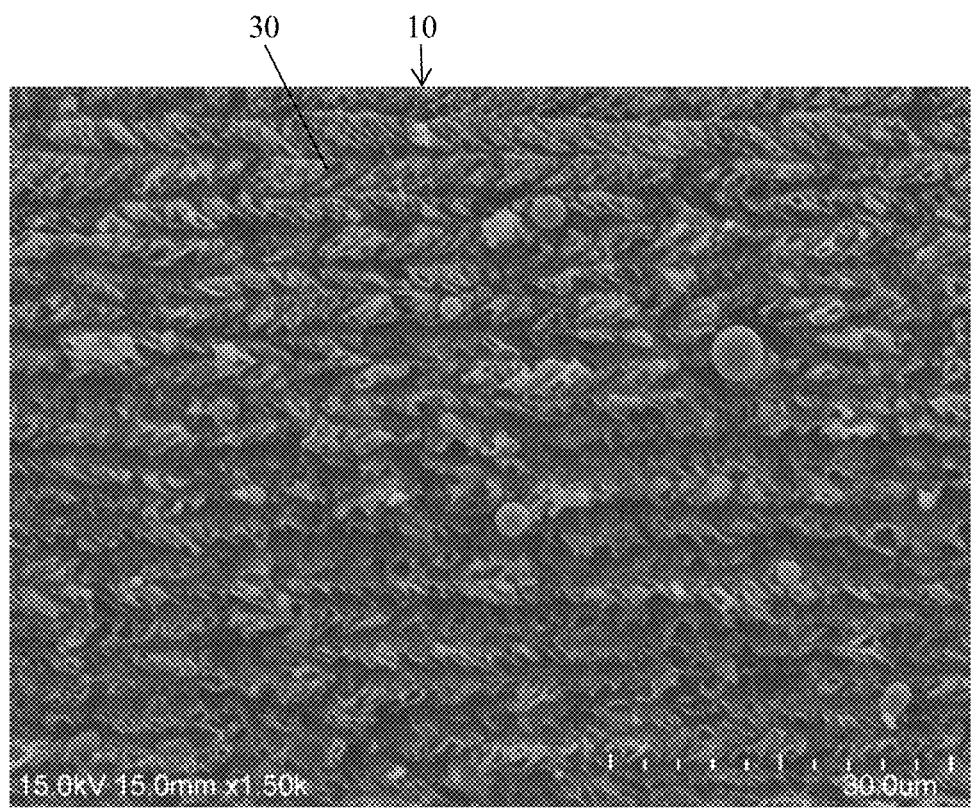
FIG. 5 is an exemplary view of an implant device with a mimetic pattern at the exposed surface.
Figure 6:
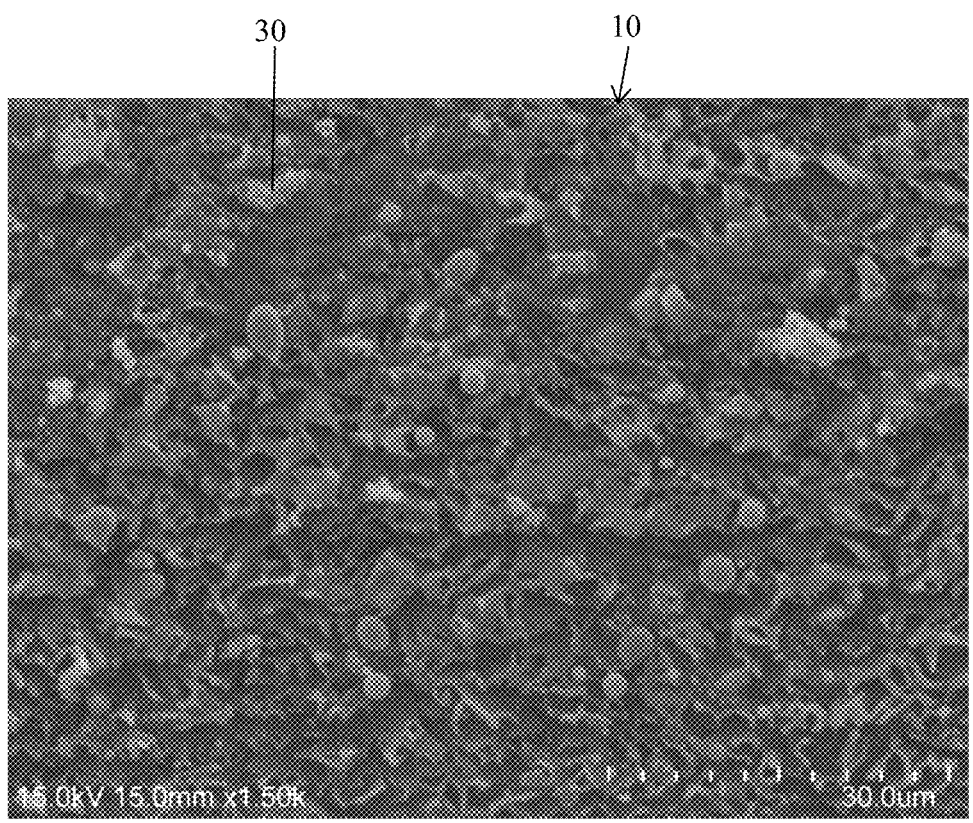
FIG. 6 is an exemplary view of the implant device of FIG. 5 wherein the exposed or exterior surfaces have the exemplary mimetic pattern underlying the conductive paths or network to provide a 3-dimensional mechanically enhanced surface with conductive features for enhanced bone growth.

FIG. 5 is a portion of an exemplary implant device with a mimetic surface treatment extending into the device several microns, greater than 5 microns to 150 microns. In these implants, the channels 21 or conductive networks 22 can be laser or other energy carved. FIG. 6 is an enlargement of FIG. 5. Once this mimetic surface is formed, the secondary step of overlaying the conductive pattern can easily be achieved by the energy exposure. The same electrically conductive paths 20 or networks 22 will easily carve the texture leaving the carbon residue in the formed channels 21 as previously discussed creating paths 20 a few microns to a millimeter wide and several microns deep to provide the electrical conductivity needed.

With reference to FIG. 7A, a chart showing Developmental Evolution (DEVO-EVO) over Time is illustrated. FIG. 7A depicts the potential over time for genetic code to be expressed and tissue differentiation to be achieved. The topology of development takes into account location, electrical charge, cell density, and time as combined elements of differentiation. Each cell type, and functionally each tissue, has a hierarchical order at what it required for differentiation. These steps are reached at different times at different associations of energy. Orange dots reflect a biologic potential, that is not restricted to cells but exists as a continuum of genetic extension resulting in distinct and characteristic expression of phenotypic—this has been referred to as morphogenetic resonance.

In FIG. 7B, the chart shows an example of Linear Development Isometric. The chart in FIG. 7B) if biologic potential is considered a grid of isobar, or proceeds on developmental landscapes with identical dimension and common electrical conductivity, tissue development can take into account a set of cues that culminates in growth in size but not in change of material until a mature sized cell, tissue, or organ has been completed.

FIG. 7C is a chart or schematic showing Epigenetic Development. FIG. 7C is another example of development, differential fields of either electrical potential or geometric identity result in contortion of the biologic potential and an epigenetic, or outside the gene, cascade. Such changes in phenotypic appearance, although bearing the same genetic code, result in diverse structural modifications; i.e. the difference between cartilage and bone although both are part of the musculoskeletal system.

FIG. 7D is representative of changes in morphology with electrical conductivity. In FIG. 7D, in line with the potential for systems to carry forward distinct patterns of morphology from identical genetic codes in an individual, an example of repeating change in morphology and electrical conductivity might result in metamerism as a final form. Such feature have been shown to develop from differential expression of growth factors, timed initiation of specific reading frames, and accountable repetition that is field induced. This morphogenetic field approach has been piloted as a theory explaining development, whereas an ability to control or convey potential in designing biologic materials has not existed in previous technologies.

In summary of FIGS. 7A-7D, cell differentiation and tissue development can proceed on lines of sensitivity that have electric domain flux, surface geometric variation, and conductivity distinctions. These lines of sensitivity can be constructed as the conductive paths 20 or networks 22 as described above. In combination, regular growth, variations in shape leading to disparity in orders of topology coupled with the distinction in electric domains sustain morphologic advantages that emerge as both genetic and epigenetic extensions.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone growth enhancing implant device comprises:
a non-conductive base structure with at least two exposed or exterior surfaces wherein at least one of the exposed or exterior surfaces has attained electrical conductivity by creating or forming conductive paths or patterns of conductive networks on at least portions of the surface by an energy exposure wherein portions of the exposed or exterior surfaces are transformed by the energy exposure to attain the electrical conductivity at the conductive paths or patterns leaving the rest of the base structure not in the paths or patterns unaltered, wherein the base structure is preferably made of an organic carbon or hydrocarbon base material composition of a synthetically produced polymer of a plastic material.

2. The bone growth enhancing implant device of claim 1 wherein the non-conductive base structure received the energy exposure in the form of a spectrum of wavelengths in the visible or non-visible range sufficient to create a material composition change to the base structure at the exposed or exterior surfaces.

3. The bone growth enhancing implant device of claim 1 wherein the material composition changes from an organic non-conductive polymer to an amorphous carbon at the conductive path or pattern.

4. The bone growth enhancing implant device of claim 3 wherein a material composition change results in a formation of conductive carbon paths or patterns formed as channels of conductive carbon residue extending at the surface to a depth of 1 to 2 or more microns occurring at the conductive paths or patterns of conductive networks.

5. The bone growth enhancing implant device of claim 4 wherein the conductive paths are formed in interconnected networks to allow electrical current to flow along the surface.

6. The bone growth enhancing implant device of claim 5 wherein the paths are small, from a few microns up to several hundred microns wide and formed in discrete channels at the surface extending to a depth of a few microns.

7. The bone growth enhancing implant device of claim 6 wherein these conductive paths react electrically to the low voltages carried by cells to enhance new bone formation at the surface of the implant device.

8. The bone growth enhancing implant device of claim 7 wherein the paths have a resistivity under 500 ohms.

9. The bone growth enhancing implant device of claim 3 wherein the material composition change results in a formation of conductive carbon paths or patterns formed as channels of conductive carbon residue extending at the surface to a depth of 1 to 2 or more microns, and that resistivity is variable, variegated, and follows domains that offer electrodynamic topology.

10. The bone growth enhancing implant device of claim 1 wherein the body structure is made of an implantable grade synthetic plastic, which is a thermoplastic or thermoset material.

11. The bone growth enhancing implant device of claim 10 wherein the plastic material can be any implantable grade material such as PEEK (polyether ether ketone), PEKK (polyether ketone ketone), polyethylene, ultra high molecular weight polyethylene, polyphenylsulfone, polysulfone, polythermide, acetal copolymer, polyester woven or solid or implantable grade lennite UHME-PE or other suitable implant material.

12. The bone growth enhancing implant device of claim 1 wherein the implant device includes anchoring holes to secure the device to the skeletal structure with fasteners or alternatively can simply be held in place by and between adjacent skeletal structures.

13. The bone growth enhancing implant device of claim 1 wherein the implant device is built by additive fabrication through a process offering reproducible and reconcilable formation to the istropic domains inherent to the marine mammal cancellous bone wherein, the internal structure is modeled for strength, neutralized for strain, and open to surface modification of its entire network of trabecular permutations.

14. The bone growth enhancing implant device of claim 1 wherein the energy used to create the conductive paths or patterns comes from a laser source.

15. The bone growth enhancing implant device of claim 14 wherein lasers provide such an energy source which occurs in a reduced oxygen environment so as to create discrete conductive paths in the absence of surface scorching, insuring the base structure is only made conductive at the paths or patterns leaving the rest of the base structure unaltered.

16. The bone growth enhancing implant device of claim 1 wherein the energy used to create the conductive paths or patterns comes from an acoustic source such as a focused acoustic lens, wherein the emitted wavelength can impinge the surface to create a chemical transformation to achieve conductive carbon residue paths or patterns.

17. The bone growth enhancing implant device of claim 1 wherein the enhanced implant device further comprises a 3-dimensional surface texture of voids at exposed surfaces that provide cell attachment locations in addition to the conductive paths wherein the combination accelerates new bone formation.

18. A bone growth enhancing implant device comprises:
a non-conductive base structure with at least two exposed or exterior surfaces wherein at least one of the exposed or exterior surfaces has attained electrical conductivity by creating or forming conductive paths or patterns of conductive networks on at least portions of the surface by an energy exposure wherein portions of the exposed or exterior surfaces are transformed by the energy exposure to attain the electrical conductivity at the conductive paths or patterns leaving the rest of the base structure not in the paths or patterns unaltered, wherein the implant device is a naturally occurring material such as an allograft bone tissue used for implantation in a mammal.

19. The bone growth enhancing implant device of claim 18 wherein the conductive paths have a resistivity under 500 ohms.

20. The bone growth enhancing implant device is made by a method having the steps of:
providing a non-conductive base structure of an implant having exterior or exposed surfaces; and
exposing at least one or more of the surfaces to an energy source to transform those surfaces of the base structure into electrically conductive paths or networks and leaving the rest of the base structure not in the paths or networks remain unaltered.

21. The method of claim 20 further includes the step of using a laser beam in an oxygen reduced environment to create amorphous carbon channels to form the conductive paths or networks.

* * * * *